United States Patent [19]

Merberg et al.

[11] Patent Number: 5,483,958
[45] Date of Patent: Jan. 16, 1996

[54] FLUORESCENT-TIPPED DOSIMETER PROBE

[75] Inventors: Glenn N. Merberg, Gaithersburg, Md.; Lothar Lilge, Hamilton, Canada

[73] Assignee: United States of America as represented by the Secretary of the Department of Health and Human Services, Washington, D.C.

[21] Appl. No.: 188,325
[22] Filed: Jan. 25, 1994
[51] Int. Cl.⁶ ............................................ A61B 5/00
[52] U.S. Cl. .......................... 128/634; 128/633; 128/665; 607/88; 250/370.07
[58] Field of Search .................. 422/82.05, 82.08, 422/82.09; 128/633–634, 664–666; 607/96, 88–95, 107; 356/436; 250/370.07

[56] References Cited

U.S. PATENT DOCUMENTS

| | | | |
|---|---|---|---|
| 4,999,306 | 3/1991 | Yafuso et al. | 128/634 |
| 4,999,504 | 3/1991 | Braunlich et al. | 250/458.1 |
| 5,045,282 | 9/1991 | Kritzman et al. | 128/634 |
| 5,102,625 | 4/1992 | Milo | 250/458.1 |
| 5,176,882 | 1/1993 | Gray et al. | 422/82.09 |
| 5,275,160 | 1/1994 | Lilge et al. | 128/634 |
| 5,330,718 | 7/1994 | Hui et al. | 128/634 |

Primary Examiner—Angela D. Sykes
Assistant Examiner—Robert L. Nasser, Jr.
Attorney, Agent, or Firm—Lowe, Price, LeBlanc & Becker

[57] ABSTRACT

A solid-state fluorescent dosimeter for monitoring therapy irradiation dosage during a photodynamic therapy procedure. The solid-state fluorescent dosimeter includes an optical fiber -having a distal end and a proximal end, and a solid-state fluorescent tip attached to the proximal end of the optical fiber. The solid-state fluorescent tip includes a fluorescent material which emits fluorescence when exposed to non-ionizing radiation in the visible or near infrared range. The solid-state fluorescent tip has a sufficient length so as ensure isotropic response characteristics to the non-ionizing radiation regardless of the orientation or alignment of the solid-state fluorescent tip relative to the irradiation source.

11 Claims, 1 Drawing Sheet

FLUORESCENT-TIPPED DOSIMETER PROBE

TECHNICAL FIELD

The present invention relates to methods and apparatuses for measuring and monitoring light irradiation dosages applied to remote situs. More particularly, the present invention relates to a fiber optical dosimetry probe for monitoring light irradiation during photodynamic therapy treatment of cancer and other diseases of neoplasm in medicine which includes a solid-state fluorescent tip.

BACKGROUND ART

A knowledge of the spacial distribution of light in tissue is of critical importance for many applications in photobiology and laser medicine. Photodynamic therapy (PDT) is a cancer treatment procedure in which a patient is injected with a photosensitizing dye. The dye injection is performed several hours to several days before photodynamic therapy is performed. This time period allows the photosensitive dye to localize and concentrate in abnormal target tissues such as cancerous tumor masses. Photodynamic therapy involves irradiation of the abnormal target tissue cells with laser light at an appropriate wavelength. This irradiation results in destruction of the targeted cells.

Under ideal conditions the use of the photosensitive dye causes the targeted tissue to be more susceptible to more susceptible to treatment irradiation. However, normal or non-targeted tissue exposed to the treatment irradiation, i.e., healthy tissue immediately surrounding a targeted tumor mass, will be destroyed if its exposure to the phototherapy irradiation exceeds a threshold value. On the other hand, if the targeted tissue does not receive sufficient phototherapy irradiation, it will not be destroyed and the therapy will not be successful. Accordingly, safe and effective application of photodynamic therapy requires accurate and adequate light delivery together with careful monitoring of the phototherapy irradiation.

The accurate measurement of light levels in a turbid media, such as cellular tissue, requires the use of a dosimetry probe that has an isotropic (angular) response. There are currently two types of isotropic dosimetry probes used in photodynamic therapy procedures.

Fiber optic dosimeter probes with highly scattering, spherical tips have been developed which exhibit approximately isotropic responses within a field that extends from the forward direction of the probe tip to about 150° from the forward direction. Such spherical-tipped probe designs provide a much weaker response to irradiation beyond about 150° from the forward direction. One disadvantage associated with spherical-tipped fiber optic dosimeter probes is that they necessarily have significantly large diameters. Typically, the sphere portions are about 800 μm in diameter and the optical fiber cores are about 400 μm in diameter. Spherical-tipped fiber optic dosimeter probes are also extremely fragile due to their size and geometry.

Fluorescent-tipped fiber optic dosimeter probes are also known to demonstrate isotropic responses. In addition, such fluorescent-tipped fiber optic dosimeter probes offer the advantage of generally having much smaller dimensions and being more rugged than spherical-tipped fiber optic dosimeter probe designs. Because of their small size, fluorescent-tipped fiber optic dosimeter probes can be inserted through hypodermic needles. Although they offer a size advantage, fluorescent-tipped fiber optic dosimeters exhibit a lower responsivity (defined as fluorescent light power per incident local fluency rate at the dosimeter probe tip) than spherical-tipped fiber optic dosimeter probes. Nevertheless, their use is often preferred in photodynamic treatment procedures in which size and strength are important considerations.

The present invention provides fiber optic dosimetry probes which have isotropic responsivities over a wide wavelength range to produce a narrow response emission and which overcome many of the disadvantages associated with prior art fiber optical dosimetry probes.

DISCLOSURE OF THE INVENTION

It is accordingly one object of the present invention to provide a fiber optic dosimeter probe.

Another object of the present invention is to provide a fiber optic dosimeter probe which has isotropic response characteristics.

It is another object of the present invention to provide a fiber optic dosimeter probe which has isotropic response characteristics over a wide wavelength range to produce a narrow response emission.

A further object of the present invention is to provide a solid-state fluorescent tip for a fiber optic dosimeter probe.

A further object of the present invention is to provide a method of monitoring irradiation at a remote situs during photodynamic therapy.

A still further object of the present invention is to provide a method of controlling treatment irradiation during a photodynamic therapy procedure.

According to these and further objects of the present invention which will become apparent as the description thereof is presented below, the present invention provides a solid-state fluorescent dosimeter which includes:

- an optical fiber having a distal end and a proximal end; and
- a solid-state fluorescent tip attached to the proximal end of the optical fiber, the solid-state fluorescent tip comprising a fluorescent material which emits fluorescence when exposed to non-ionizing radiation in the visible or near infrared range, the solid-state fluorescent tip being of a sufficient length so as to have isotropic response characteristics to the non-ionizing radiation.

The present invention further provides an apparatus for performing photodynamic therapy which includes:

- at least one irradiation treatment light source for delivering therapy irradiation to a remote situs;
- at least one solid-state fluorescent dosimeter including an optical fiber having a distal end and a proximal end, and a solid-state fluorescent tip attached to the proximal end of the optical fiber, the solid-state fluorescent tip comprising a fluorescent material which emits fluorescence when exposed therapy irradiation from the at least one irradiation treatment light source, the solid-state fluorescent tip being of a sufficient length so as to have isotropic response characteristics to therapy irradiation produced from the at least one irradiation treatment light source; and
- a spectral analyzer to which the distal end of each optical fiber is attached.

Moreover, the present invention also provides a method of monitoring photodynamic therapy which involves:

- directing therapy irradiation to a target tissue;
- providing at least one solid-state fluorescent dosimeter including an optical fiber having a distal end and a proximal end, and a solid-state fluorescent tip attached to the proximal end of the optical fiber, the solid-state fluorescent tip comprising a fluorescent material which emits fluorescence when exposed to the treatment irradiation, the solid-state fluorescent tip being of a sufficient length so as to have isotropic response characteristics to the treatment irradiation;

positioning the at least one solid-state fluorescent dosimeter near or within the target tissue so that the solid-state fluorescent tip of the at least one solid-state fluorescent dosimeter receives the therapy irradiation; and detecting changes in fluorescence emitted by the fluorescent material.

BRIEF DESCRIPTION OF DRAWINGS

The present invention will be described with reference to the attached drawings which are given by way of non-limiting examples only, in which.

BEST MODE FOR CARRYING OUT THE INVENTION

Figure 1:
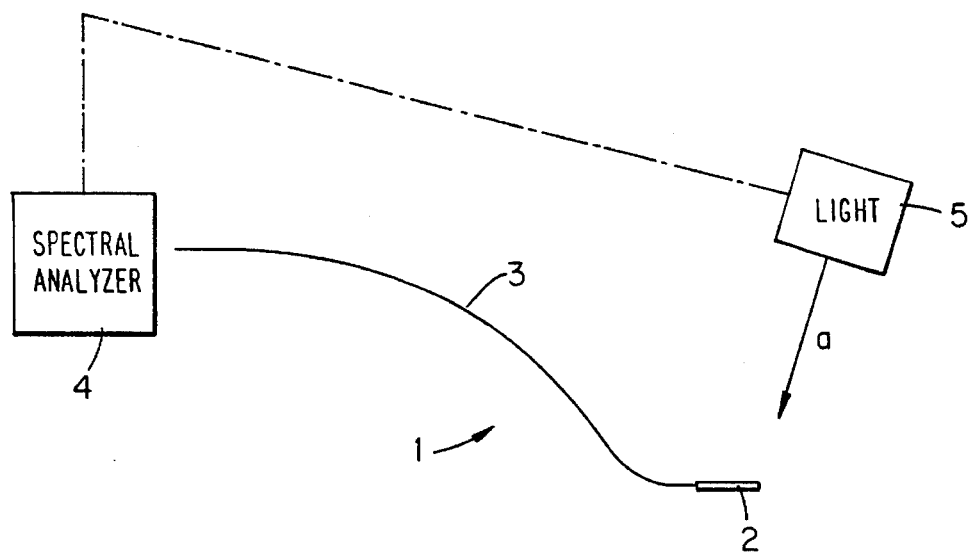
FIG. 1 is a schematic diagram of a fiber optic dosimeter probe according to one embodiment of the present invention.

The present invention is directed to methods and apparatuses for measuring light levels at a remote situs, or more preferably at various positions in cellular tissue structures or other turbid media. According to the present invention a fiber optic dosimeter probe is provided which exhibits an isotropic response. Because of the isotropic response characteristics of the probe, the probe can be used to accurately measure fluence rate in a remote situs regardless of the probe's orientation or alignment relative to the light source. In addition, simultaneous monitoring of fluorescence from exogenous chromophores such as conventional photosensitizers can be performed. Such information can be used to monitor the concentration and/or photobleaching of the exogenous chromophores. The ability to preform such multitask functions is due to the fact that the fluorescent intensity of a photosensitizer chromophore is proportional to the intensity of the excitation light, the fluorescence quantum yield of the fluorophore in a given chemical environment, and the concentration of the chromophore. Assuming that the fluorescence quantum yield of the chromophore of interest is known, the concentration of the chromophore can be calculated from the measured local fluence rate and the local fluorescence intensity. The simplest manner of simultaneously monitoring fluence rate and fluorescence dosimetry of exogenous chromophores is to utilize a beam splitter in conjunction with a long-pass filter (to separate the fluorescent-tip emission from other fluorescence) at the distal end of the optical fiber to send the emerging light to both a photodiode for fluence rate measurements and to an optical multichannel analyzer for fluorescence dosimetry of the exogenous chromophores.

When one or more of the fiber optic dosimeter probes of the present invention are implanted into tumor structures, the fiber optic dosimeter probes can provide the clinician with a measurement of the actual dose of treatment irradiation while it is being delivered to various locations within the tumor where the probes are located. Using several of the fiber optic dosimeter probes positioned in and around the target tissue allows the clinician to apply photodynamic therapy much more safely and effectively, thereby ensuring adequate irradiation to destroy a target tissue, while avoiding or minimizing harm to surrounding healthy normal tissue.

The fiber optic dosimetry probes of the present invention allow spontaneous or real-time monitoring of treatment irradiation during photodynamic therapy procedures and concentration and/or photobleaching of exogenous chromophores such as photosensitizers. According to the present invention the real-time monitoring of the fluence distribution during treatment can be used to adjust the light dose as the optical properties of the tissue change during treatment. In addition, the irradiation dosage measured or monitored by one or more of the implanted probe tips can be used to adjust, regulate or terminate therapy irradiation applied to the target situs from one or more light sources.

The fiber optic dosimeter probes of the present invention provide several advantages over prior art fluorescent-tipped fiber optic dosimeter probes. In contrast to known fluorescent-tipped fiber optic dosimeter probes which incorporate dye-loaded sensor tips, the fiber optic dosimeter probes of the present invention are completely solid-state.

Solid-state fluorescence has the advantage of exhibiting responses to a wide wavelength range to produce a narrow response emission as compared to dye fluorescence. Because the solid-state fluorescent response of the fiber optic dosimeter probes of the present invention is spectrally narrow, it is easy to discriminate fluorescence generated by the probe tip from any background fluorescence which is generated by the photosensitizer dye and collected by the probe. Thus, spectral analysis of the probe signal provides information about real-time light delivery as well as changes, e.g, photobleaching of the photosensitizer present in the target tissue. This gives the clinician two distinct dosimetry measurements, and allows for the assessment of therapy effectiveness as a function of time.

The fluorescent emission response of the fiber optic dosimeter probes of the present invention ranges from about 600 nm to about 2000 nm. In comparison, background fluorescence generated by the photosensitizer present in the target tissue can range from 630 nm to 750 nm. Treatment irradiation used in photodynamic therapy procedures is generally in the range of 630 nm to 750 nm.

According to one embodiment of the present invention, the fiber optic dosimeter probes are used to preform real-time thermometry at implanted tissue locations. Such thermometry has been determined to be possible due to the fact that solid-state fluorescence is often spectrally shifted by small changes in temperature. Accordingly, by detecting shifts that occur in the narrow line width of the emission, it is possible to perform real-time thermometry on tissue structures during the irradiation. This feature of the present invention which is not provided by prior art devices is important because of the effect of heat in photodynamic therapy treatment procedures.

According to the present invention, treatment irradiation and heat effects can be simultaneously monitored by detecting the signal strength of the fluorescence produced in the probe tip and by detecting any spectral shifts in this fluorescence. The fact that the fiber optic dosimeter probes of the present invention have isotropic responsivities over a wide wavelength range to produce narrow response emissions allows for such simultaneous monitoring.

In contrast to probes that incorporate fluorescent dyes, solid-state fluorescers are not susceptible to photobleaching.

Photobleaching of fluorescent dyes is caused when fluorescent species or fluorophores absorb irradiation energy and are annihilated, resulting in a decrease in concentration of the fluorescent species. When photobleaching occurs in fluorescent dyes which are incorporated in fluorescent dosimeters, the responsivity of the dosimeters decreases over time as the concentration of the fluorescent species decreases. When photobleaching occurs in dosimeters, it is necessary to repeatedly calibrate the dosimeters for each use. In contrast, the solid-state fiber optic dosimeter probes of the present invention, which are not susceptible to photobleaching, have a constant response after repeated use and therefore, can be pre-calibrated at the time they are manufactured.

FIG. 1 is a schematic diagram of a fiber optic dosimeter probe according to one embodiment of the present invention. In FIG. 1 the fiber optic dosimeter 1 includes a solid-state fluorescent tip 2 which is connected to a suitable length of optical fiber 3. The length of the optical fiber 3 is chosen so that the solid-state fluorescent tip 2 can be positioned in a desired tissue situs and connected to a spectral analyzer 4. The spectral analyzer 4 is chosen from commercially available spectral analyzers which can detect and discern different fluorescent emissions and shifts in fluorescent emissions when the dosimeters are to be used for thermometry.

In use, the solid-state fluorescent tip 2 of the fiber optic dosimeter 1 is positioned in a remote situs whereat irradiation intensity is to be measured. In FIG. 1 treatment irradiation is directed in the direction of arrow "a" from a conventional light source, e.g. an argon laser, utilizing optical fibers or otherwise comprises surface illumination. In the case of photodynamic therapy treatment of a solid tumor mass, probes may be inserted through hypodermic needles, cannulas, or the like, at several locations in and around the tumor mass. When the irradiation therapy light strikes the solid-state fluorescent tips of the implanted probes, the probe tips fluoresce. The fluorescent signal from each probe is conducted through the optical fiber 3 attached to the solid-state fluorescent probe tip and received by the spectral analyzer 4. Although FIG. 1 shows a single fiber optic dosimeter 1, it is to be understood that more than one fiber optic dosimeter 1 can be used at a time.

In the case of photodynamic therapy, the photosensitizing dye adsorbed in the target tissue will fluoresce. In such an instance, the fluorescence generated by the photosensitive dye will be received by the solid-state fluorescent probe tip 2 and conducted to the spectral analyzer 4 together with the fluorescent signal generated in the solid-state fluorescent probe tip 2.

Because the fluorescent response of the fiber optic dosimeter probes 1 of the present invention is spectrally narrow, it is easily discriminated from the fluorescence produced by the photosensitizing dye which has been adsorbed in the tissue surrounding or near the implanted solid-state fluorescent probe tip.

The spectral analyzer 4 may include various conventional elements known to spectrally discriminate different wavelengths, such as diffraction gratings, prisms, and the like, which are integrated in a known manner with an array of conventional detectors, e.g. a ccd camera. Alternatively, a scanning spectral analyzer may be used in place of a detector array in a conventional manner. These exemplary elements which may be incorporated in the spectral analyzer 4 are conventional and therefore not shown in the drawings.

For purposes of monitoring phototherapy treatment, the spectral analyzer 4 can display an output which is indicative of spontaneous or real-time treatment irradiation and/or real-time thermometry of tissue structures. Such information can be provided by conventional calibration techniques. It is also possible to determine and display cumulative treatment irradiation by integrating the fluorescence signal over time.

According to another embodiment of the present invention, the spectral analyzer 4 can provide an output signal which is used to control, e.g., adjust, regulate or terminate therapy irradiation applied from one or more treatment irradiation sources 5. Such control is depicted by the dashed line in FIG. 1 which connects between the spectral analyzer 4 and the phototherapy irradiation light source 5.

Figure 2:
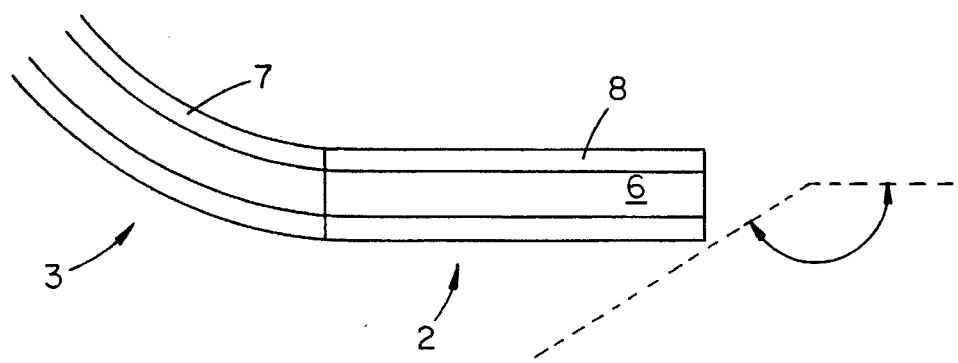
FIG. 2 is a schematic planar view of the tip of the fiber optic dosimeter probe according to one embodiment of the present invention.

FIG. 2 is a schematic planar cross sectional view of the solid-state fluorescent tip of the fiber optic dosimeter probe according to one embodiment of the present invention. The solid-state fluorescent tip 2 of the fiber optic dosimeter probe 1 includes a short length of a doped-core optical fiber 6 attached to an proximal end of an undoped optical fiber 3 which delivers a fluorescent signal received by the doped-core optical fiber 6 to the spectral analyzer 4 to which the distal end of the optical fiber 3 is attached.

The doped-core section of the probe tip acts as the solid-state fluorescence. The dopant material is selected from rear-earth elements or any ionic species known to fluoresce when irradiated with the particular treatment light which the dosimeter is to detect. Dopant materials which have been found to be particular useful for purposes of the present invention include $Nd^{3+}$, $Cr^{3+}$ and $Er^{3+}$. These materials can be used to detect treatment irradiation over a range of about 500 nm to 700 nm. This range encompasses all conventionally used phototherapy irradiation wavelengths. In addition, the long Stokes shift (e.g. $\lambda fl \geq 200$ nm for rare earth doped silica), enables simultaneous collecting of information from endogenous or exogenous chromophores in a target tissue by Raman and/or fluorescence spectroscopy.

The optical fiber 3 can be made of any conventional material including, for example fused silica, quartz, PCS, plastic, and the like. The optical fiber 3 is preferably covered with a cladding material 7 which ensures total internal reflection of the fluorescent signal which is transferred through the optical fiber 3. Any conventional cladding material can be used which contains the fluorescent signal. The cladding material is preferably biocompatable.

The doped-core optical fiber 6 can be made of the same material as the optical fiber 3. The doped-core optical fiber can be produced by rendering the core material porous and contacting the porous core with a solution containing the dopant ions as discussed in detail below. In an alternative embodiment, the doped core optical fiber can be produced by utilizing conventional ion implantation techniques on a length of the core material. As shown in FIG. 2, the doped-core optical fiber 6 can be covered with a transparent material 8 such as plastics, glasses, and the like. One example of a doped-core optical fiber tested during the course of the present invention was an $Nd_{3+}$ doped phosphate laser glass obtained from Schott Glass (LG-750, Schott Glass, Duryes, Penna.). The $Nd_{3+}$ doping concentration was 0.7 percent weight oxide, with a fluorescent quantum yield $\theta_f \sim 0.85$ and a fluorescent lifetime $T_f \sim 350$ µsec for 500 nm excitation light. This doped core fiber was epoxy fused to a silica optical fiber.

As an alternative to utilizing a doped-core optical fiber, a short section of a known fluorescent crystal, such as a ruby crystal, can be attached to the end of the optical fiber 3. Such a fluorescent crystal can be attached to the optical fiber by various conventional means, including optical cementS, or mechanical securing means, e.g., cylindrical sleeves of transparent materials.

It is important that the doped-core optical fiber 6 (or the fluorescent crystal) have a sufficient aspect ratio (length to diameter) to assure isotropic response of the probe. That is, the length, in relationship to the diameter, must be sufficient to receive irradiation regardless of the orientation thereof with respect to the source of irradiation. Ideally, the aspect ratio should be sufficient to ensure isotropic response characteristics within a field that extends from the forward direction of the probe tip to about 170° from the forward direction (see phantom depiction in FIG. 2). This field provides a sufficient or substantially isotropic response so that a single dosimeter could be used to accurately monitor local fluence rate. For doped-core optical fibers, the doped portion should have an aspect ratio of at least 1.5 and preferable between about 1.5 to 2.0. A similar aspect ratio applies to fluorescent crystals. In all cases, the diameter of the optical fiber, and probe tip, should be less than 200 μμm, and preferably between 170 μm and 100 μ m. Although the dimensions of the fiber optic dosimeter probe should be minimized for in vivo use, there is no limit, other than a practical limit, on the upper size of the probe elements.

The fluorescent species or fluorescent crystal used in the probe tip is selected to have a detectable response for the wavelength of light to be measured. In this regard, it is noted that the fiber optic dosimeter probes of the present invention are designed to monitor low energy photons, i.e., irradiation in the visible and near infrared range (non-ionizing radiation), which are conventionally used in photodynamic therapy.

The doped-core optical fiber tips used according to the present invention can be attached to the optical fibers by known fusion-splicing techniques or other known techniques, including friction welding, the use of optical cements, etc. Because the materials used in the doped-core fiber tip can be the same or essentially the same as the material from which the optical fiber is constructed, the fluorescent tip can treated as an optical fiber so that conventional optical fiber splicing techniques can be used to fix the tip to the optical fiber. Such conventional optical fiber splicing techniques will produce solid-state probes with much better strength than either conventional dye-loaded tips or spherical-tipped probes.

According to another embodiment of the present invention, the doped-core fiber can be made by removing, e.g. etching, the cladding from one end of the optical fiber 3, rendering the exposed core portion of the optical fiber porous, and impregnating the fluorescent dopant in the porous core. The core can be made porous by utilizing a suitable solving solution at proper conditions to leach out material from the core. For example, a sodium borosilicate glass fiber core can be phase separated by heating at 560° C. The borate rich phase can then be leached out utilizing a solution of hydrochloric acid. The resulting porous core can thereafter be contacted with a solution containing the desired fluorescent dopant by a dipping process, or other coating process.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. In a fluorescent dosimeter having an optical fiber with a proximal end and a distal end, the improvement comprising:

a solid-state fluorescent tip attached directly to the proximal end of the optical fiber so that said solid- state fluorescent tip is in direct contact with the proximal end of the optical fiber, said solid-state fluorescent tip comprising a fluorescent material which emits fluorescence when exposed to non-ionizing radiation in the visible or near infrared range, said solid-state fluorescent tip being of a sufficient length so as to have a substantially isotropic response characteristics within a field that extends from a forward direction of said solid-state tip up to about 170° from said forward direction to the non-ionizing radiation.

2. A fluorescent dosimeter according to claim 1, wherein said solid-state fluorescent tip has an aspect ratio which is at least about 1.5.

3. Fluorescent dosimeter according to claim 1, wherein said solid-state fluorescent tip comprises a matrix which is impregnated with said fluorescent material.

4. A fluorescent dosimeter according to claim 3, wherein said fluorescent material comprises a fluorophore which is not photobleachable by non-ionizing radiation in the visible or near infrared range.

5. A fluorescent dosimeter according to claim 4, wherein said fluorescent material comprises an ion of a rare earth element.

6. A fluorescent dosimeter according to claim 3, wherein said matrix comprises a porous extension of said optical fiber.

7. A fluorescent dosimeter according to claim 1, wherein said solid state fluorescent tip comprises a crystalline material which emits fluorescence when exposed to non-ionizing radiation in the visible or near infrared range.

8. A fluorescent dosimeter according to claim 7, wherein said crystalline material comprises a ruby crystal.

9. A fluorescent dosimeter according to claim 1, wherein said optical fiber is covered with a cladding layer and said solid-state fluorescent tip is covered with a transparent covering.

10. In a system for performing photodynamic therapy which includes at least one fluorescent dosimeter having an optical fiber with a proximal end and a distal end and at least one irradiation treatment light source for delivering therapy irradiation to a remote situs, the improvement comprising:

a solid-state fluorescent tip attached directly to the proximal end of the optical fiber so that said solid-state fluorescent tip is in direct contact with the proximal end of the optical fiber, said solid-state fluorescent tip comprising a fluorescent material which emits fluorescence when exposed to therapy irradiation from said at least one irradiation treatment light source, said solid-state fluorescent tip being of a sufficient length so as to have a substantially isotropic response characteristic, within a field that extends from a forward direction of said solid-state tip up to about 170° from said forward direction to therapy irradiation produced from said at least one irradiation treatment light source; and a spectral analyzer to which the distal end of said at least one optical fiber is attached.

11. A system for performing photodynamic therapy according to claim 10, wherein said spectral analyzer includes means to control the output of said at least one irradiation treatment light source.

* * * * *